(12) United States Patent
Sos

(10) Patent No.: US 11,376,400 B2
(45) Date of Patent: Jul. 5, 2022

(54) UPPER EXTREMITY ACCESS ANGIOGRAPHIC CATHETER

(71) Applicant: Thomas A. Sos, New York, NY (US)

(72) Inventor: Thomas A. Sos, New York, NY (US)

( * ) Notice: Subject to any disclaimer, the term of this patent is extended or adjusted under 35 U.S.C. 154(b) by 0 days.

(21) Appl. No.: 17/001,950

(22) Filed: Aug. 25, 2020

(65) Prior Publication Data

US 2021/0077779 A1 Mar. 18, 2021

Related U.S. Application Data

(60) Provisional application No. 62/891,592, filed on Aug. 26, 2019.

(51) Int. Cl.
*A61M 25/01* (2006.01)
*A61B 6/00* (2006.01)
*A61M 25/00* (2006.01)
*A61M 25/09* (2006.01)

(52) U.S. Cl.
CPC .... *A61M 25/0133* (2013.01); *A61M 25/0045* (2013.01); *A61M 25/0068* (2013.01); *A61M 25/09* (2013.01); *A61B 6/504* (2013.01); *A61M 2210/125* (2013.01)

(58) Field of Classification Search
CPC .......... A61M 25/0133; A61M 25/0068; A61M 25/09; A61M 25/0141; A61M 25/007; A61B 6/504
See application file for complete search history.

(56) References Cited

U.S. PATENT DOCUMENTS

| 4,033,331 | A | | 7/1977 | Guss et al. | |
|---|---|---|---|---|---|
| 5,215,540 | A | * | 6/1993 | Anderhub | A61M 25/0041 604/264 |
| 5,536,261 | A | * | 7/1996 | Stevens | A61M 25/0068 604/256 |

(Continued)

FOREIGN PATENT DOCUMENTS

WO WO-2006019640 A1 2/2006

OTHER PUBLICATIONS

PCT/US20/47843 Search Report & Written Opinion dated Nov. 20, 2020.

*Primary Examiner* — Nathan R Price
*Assistant Examiner* — Tasnim Mehjabin Ahmed
(74) *Attorney, Agent, or Firm* — Wilson Sonsini Goodrich & Rosati

(57) ABSTRACT

Catheters with at least two curved portions near their distal ends are provided. The lengths and/or curvatures of the curved portions are selected so that a catheter can be advanced through a brachiocephalic or left subclavian artery (BCA or LSC) to access the ascending or descending aorta (AA or DA), withdrawn therefrom, and simply rotated to access the AA or DA. Hence, the catheters provide access to both the AA and DA through the BCA or LSC without any need to withdraw the catheter from the BCA or LSC, e.g., so a second catheter can be exchanged for it. The catheter can further be advanced through the DA into the abdominal aorta and rotated to access branch arteries including the vessels of the lower extremities. The catheters are usable for flush aortography, arteriography, and intravascular pressure measurements, and can be introduced to the BCA or LSC via radial artery access.

13 Claims, 17 Drawing Sheets

(56) References Cited

U.S. PATENT DOCUMENTS

| | | | |
|---|---|---|---|
| 5,876,385 A * | 3/1999 | Ikari | A61M 25/0041 |
| | | | 604/523 |
| 5,885,247 A | 3/1999 | Slagboom | |
| 5,957,911 A | 9/1999 | Nesto | |
| 6,086,548 A | 7/2000 | Chaisson et al. | |
| 6,132,417 A | 10/2000 | Kiesz | |
| 6,335,026 B1 | 1/2002 | Katayama et al. | |
| 6,355,026 B1 | 3/2002 | Mick | |
| 7,799,013 B2 | 9/2010 | Gandras | |
| 8,100,883 B1 | 1/2012 | Johnson | |
| 8,353,849 B2 | 1/2013 | Tamai et al. | |
| 8,403,912 B2 | 3/2013 | McFerran et al. | |
| 8,753,329 B2 | 6/2014 | Johnson | |
| 10,052,456 B1 | 8/2018 | Chiu et al. | |
| 2006/0089618 A1 | 4/2006 | McFerran et al. | |
| 2006/0161177 A1 | 7/2006 | Worley et al. | |
| 2013/0190619 A1 | 7/2013 | Nudel | |
| 2016/0136394 A1 * | 5/2016 | Kobayashi | A61M 25/0147 |
| | | | 604/510 |

* cited by examiner

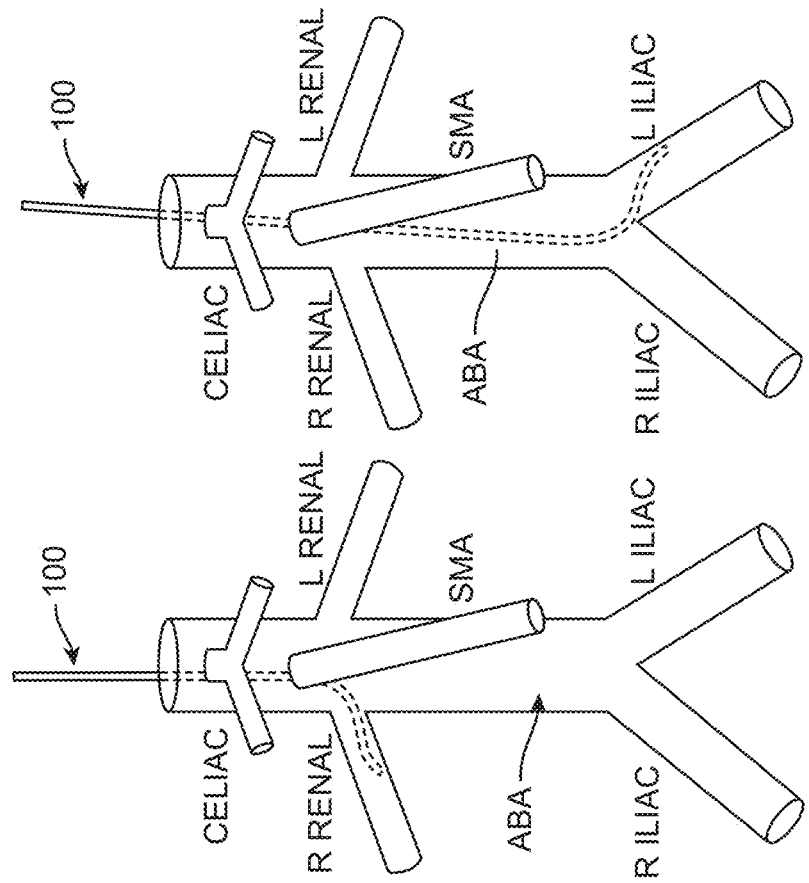
FIG. 8C
FIG. 8B
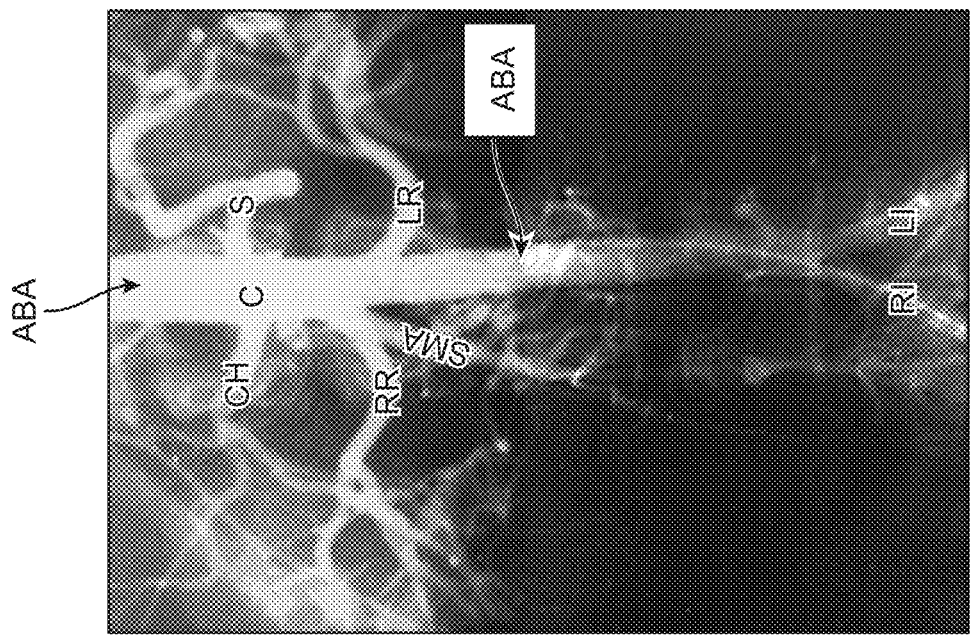
FIG. 8A

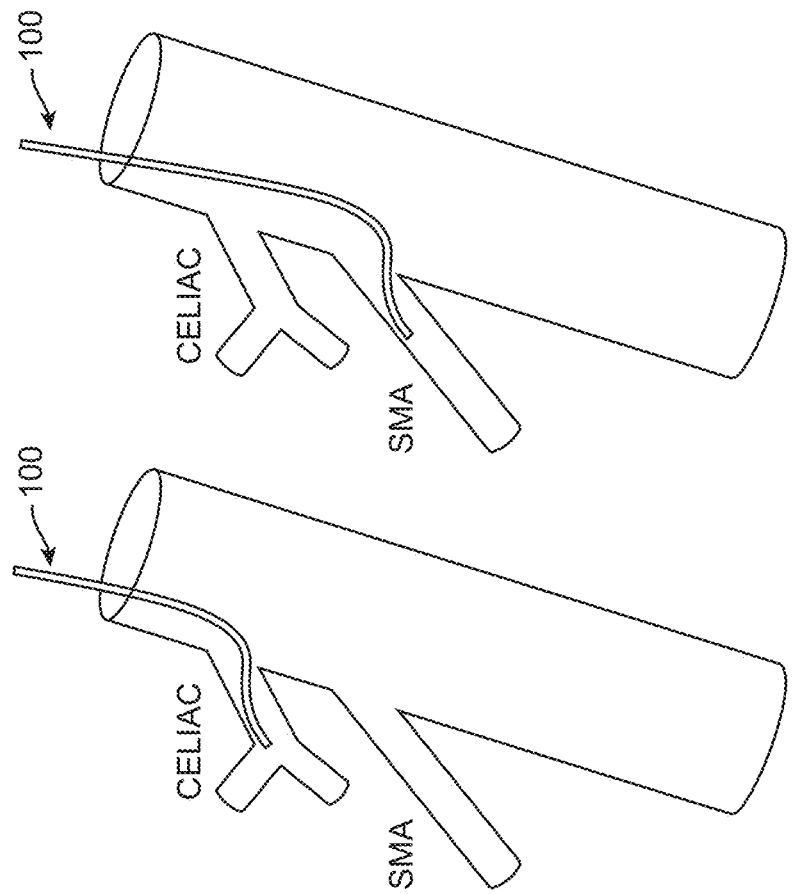
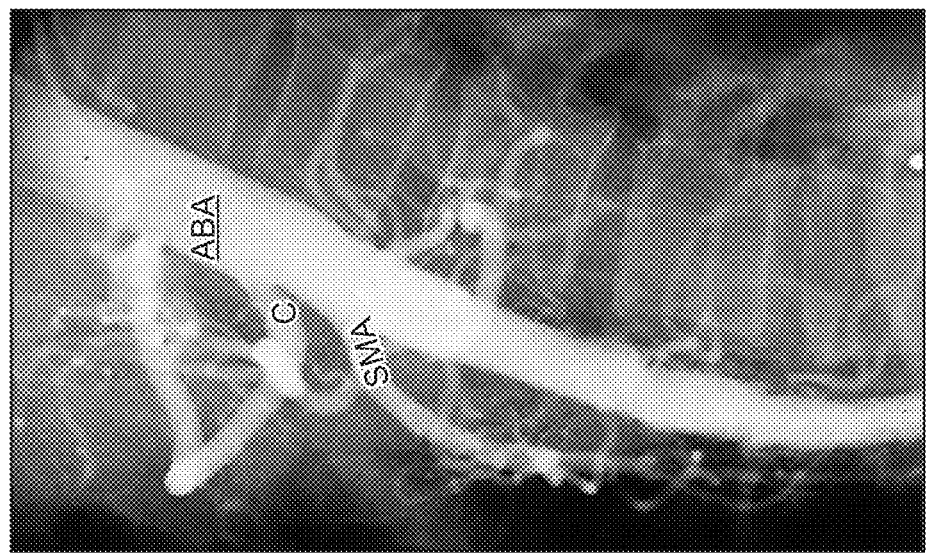
FIG. 9A  FIG. 9B  FIG. 9C

UPPER EXTREMITY ACCESS ANGIOGRAPHIC CATHETER

CROSS-REFERENCE

This application claims the benefit of U.S. Provisional Application No. 62/891,592, filed Aug. 26, 2019, the entire disclosure of which is incorporated herein by reference.

BACKGROUND

Catheters are commonly used, tube-like medical devices used to access various lumens and passages in the body while minimizing disruption to other tissue. One common use of catheters is to access the circulatory system, or any body cavity or organ usually through a needle puncture, from which access site the catheter is navigated to a target site for a treatment or diagnostic procedure. The access site can be in any number of locations. Common access locations are a femoral artery, a femoral vein, a brachial artery, a radial artery, a carotid artery, a brachial vein, a jugular vein, or through the skin directly into body cavities and organs to name a few. The location of the access site can be chosen based on many considerations, including the injury risk to the nearby anatomy, the injury risk to the vasculature, body cavity, or organ that needs to be navigated to, the difficulty of navigating the catheter to the target location, the number of catheter exchanges required, and the number and type of catheter manipulations required, to name a few.

One common access site is the radial artery. Radial access has been known for at least 25 years. The radial access catheters that are commercially available, however, are configured for only coronary applications. Hence, the use of radial access for peripheral vascular applications has been limited by having to use catheters designed for coronary applications or peripheral vascular catheters designed for transfemoral access. Also, many commercially available catheters are provided in flush or selective configurations, but not both or not for both flush and selective application in a single configuration. Hence, it is often the case that a catheter for one purpose needs to be exchanged (e.g., retracted and replaced) for another catheter for a different purpose to complete a procedure. This need for catheter exchange complicates and prolongs the procedure and increases the risk of injury to the patient. Hence, safer, more easily used and manipulated catheters, and more multi-functional catheters which require fewer exchanges may be desirable.

References of interest include: WO2006019640, US20130190619, U.S. Pat. Nos. 8,753,329, 8,403,912, 8,353,849, 7,799,013, 6,335,026, 6,132,417, 6,086,548, 5,957,911, 5,876,385, 5,215,540, and 4,033,331.

SUMMARY

The present disclosure is related to medical devices and methods, particularly catheters. Catheters with at least two curved portions near their distal ends are provided. The catheters can be advanced to either the brachiocephalic or left subclavian artery, typically via radial artery access. The lengths of the straight and curved portions and the curvatures of the curved portions are selected so that after a guidewire is initially advanced through the right brachiocephalic or left subclavian artery to access the ascending or descending thoracic aorta, the catheter can be introduced over the guidewire into the ascending or descending aorta, retracted therefrom, and simply rotated to access the descending or ascending aorta, respectively. From the descending aorta, the abdominal aorta and its branch arteries, the iliac arteries, and the arteries of the lower extremities may be conveniently accessed as well. The catheters may be used for flush aortography, selective and subselective branch catheterization, or both. Hence, the catheters provided herein perform many functions:

1. Through the right brachiocephalic or left subclavian artery, they may provide access to both the ascending and descending aorta and further, be advanced through the descending aorta into the abdominal aorta and its branches including to the lower extremity circulation.
2. The same catheter may be used for aortic flush injections.
3. The same catheter may be rotated and manipulated to access any number of selective or sub-selective branch arteries including those of the lower extremities.
4. The same catheter may be used for selective or subselective arteriograms or intravascular pressure measurements.

All these functions may be performed by a single catheter without any need for catheter exchange, e.g., withdrawing the catheter from any location so a second or further catheter with different functionality may be introduced in its place.

Aspects of the present disclosure provide catheters for accessing the ascending aorta and the descending aorta of a patient without removal from the brachiocephalic or left subclavian artery. An exemplary catheter may comprise (i) a distal end portion, (ii) a first curved portion proximal of the distal end portion, the first curved portion being biased to be curved with a first radius of curvature from 5 to 20 mm, (iii) a curve transition portion proximal of the first curved portion, (iv) a second curved portion proximal of the transition portion, the second curved portion being biased to be curved in a direction opposite the first curved portion and with a second radius of curvature from 5 to 15 mm, and (v) an elongate portion proximal of the second curved portion.

The distal end portion of the catheter may comprise an atraumatic tip or may be tapered. The elongate portion of the catheter may be biased to be straight. The catheter may further comprise a guidewire lumen, one or more side ports, and/or a hydrophilic coating. Typically, an outer diameter of the catheter may be between 3 and 8 Fr, and an inner diameter of the catheter may be between 0.018" and 0.038". The catheter may have an overall length of between 100 and 150 cm. The elongate portion may have a length of at least 80 to 200 cm, or a length in a range between 80 to 200 cm.

A first embodiment of the catheters may be provided. This first embodiment may have the following dimensions. The distal end portion may have a length of 1 to 7 mm, preferably 2 to 6 mm, for example, 2.5 mm. The transition portion may have a length of 1 to 8 mm, preferably 2 to 7 mm, for example, 2.5 mm. The first curved portion may have a length of 2 to 8 mm, preferably 3 to 7 mm, for example, 4 mm. The second curved portion may have a length of 4 to 20 mm, preferably 5 to 17 mm, for example, 14 mm. The first radius of curvature of the first curve portion may be from 5 to 20 mm or 10 to 20 mm, preferably 12 to 17 mm, for example 14.5 mm or 15 mm. The second radius of curvature of the second curved portion may be from 7 to 15 mm, preferably 8 to 13 mm, for example, 11 mm. The first curved portion may have a curvature of 10° to 30°, preferably a curvature of 12° to 17°, for example, a curvature of 15°. The second curved portion may have a curvature of 50° to 90°, preferably a curvature of 60° to 80°, for example, a curvature of 74°. The distal end portion may have an angle of 120° to 170° relative to the curve transition portion, preferably an angle of 140° to 160°, for example, and angle of 155°. The curve transition portion may have an angle of 90° to 125° relative to the elongate portion, preferably an angle of 95° to 115°, for example, an angle of 105°. The distal end portion may have an angle of 95° to 150° relative to the elongate portion, preferably an angle of 105° to 140°, for example an angle of 130°.

A second embodiment of the catheters may be provided. This second embodiment may have the following dimensions. The distal end portion may have a length of 1 to 7 mm, preferably 2 to 6 mm, for example, 6 mm. The transition portion may have a length of 2 to 10 mm, preferably 3 to 9 mm, for example, 8 mm. The first curved portion may have a length of 3 to 12 mm, preferably 4 to 11 mm, for example, 6 mm. The second curved portion may have a length of 3 to 15 mm, preferably 4 to 12 mm, for example, 8 mm. The first radius of curvature of the first curve portion may be from 5 to 15 mm, preferably 6 to 13 mm, for example 8.2 mm. The second radius of curvature of the second curved portion may be from 5 to 15 mm, preferably 6 to 13 mm, for example 8.25 mm. The first curved portion may have a curvature of 20° to 60°, preferably a curvature of 30° to 50°, for example, a curvature of 40°. The second curved portion may have a curvature of 20° to 60°, preferably a curvature of 30° to 50°, for example, a curvature of 36°. The distal end portion may have an angle of 110° to 160° relative to the curve transition portion, preferably an angle of 120° to 155°, for example, an angle of 143°. The curve transition portion may have an angle of 110° to 160° relative to the elongate portion, preferably an angle of 120° to 155°, for example an angle of 142°. The distal end portion may have an angle of 80° to 130° relative to the elongate portion, preferably an angle of 90° to 120°, for example, an angle of 103°.

Aspects of the present disclosure provide methods of accessing an ascending aorta and a descending aorta of a patient. An exemplary method may comprise the steps of (i) advancing a catheter through a subclavian artery so that a distal tip of the catheter is at or adjacent the ascending aorta or the descending aorta, with a distal port of the catheter oriented toward the ascending aorta or the descending aorta, and (ii) rotating the catheter about its longitudinal axis such that the distal port of the catheter is oriented toward the other of the ascending aorta or the descending aorta.

The subclavian artery may be the left subclavian artery or the brachiocephalic artery.

The method may further comprise a step of advancing a guidewire into the ascending aorta or the descending aorta with the distal port of the catheter oriented toward the ascending aorta or the descending aorta.

The method may further comprise a step of further advancing the catheter into the ascending aorta or the descending aorta with the distal port of the catheter oriented toward the ascending aorta or the descending aorta.

The method may further comprise a step of advancing a guidewire into the other of the ascending aorta or the descending aorta with the distal port of the catheter oriented toward the other of the ascending aorta or the descending aorta.

The method may further comprise a step of further advancing the catheter into the other of the ascending aorta or the descending aorta with the distal port of the catheter oriented toward the other of the ascending aorta or the descending aorta.

The method may further comprise a step of comprising advancing the catheter through a radial artery into the brachiocephalic or left subclavian artery. The catheter may be advanced through the radial artery via an access site at a wrist of the patient.

The other of the ascending aorta or the descending aorta may be the descending aorta, and the method may comprise further advancing the catheter into the abdominal aorta through the descending aorta. The method may further comprise a step of rotating the catheter about the longitudinal axis thereof to position the distal port of the catheter to face the celiac artery, the superior mesenteric artery, the right renal artery, the left renal artery, the hepatic artery, or the like of the patient. The method may further comprise a step of positioning the distal port of the catheter to face a first renal artery ostium and advancing a guidewire into a first renal artery. The method may further comprise a step of rotating the catheter so that the distal port of the catheter faces a second renal artery ostium and advancing a guidewire into the second renal artery.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-3C show a straightening "stiff" tip guidewire being advanced through the catheter; FIGS. 3D-3E show a non-straightening "floppy" soft tip guidewire being advanced through the catheter;

FIG. 8A shows a frontal arteriographic image of the abdominal aorta and major branch arteries including the iliac arteries;

FIG. 8B shows a schematic frontal image of the abdominal aorta and major branch arteries, as well as the catheter of FIG. 1A or FIG. 2A being used to access the right renal artery from the suprarenal abdominal aorta, according to embodiments of the present disclosure;

FIG. 8C shows a schematic frontal image of the abdominal aorta and major branch arteries, as well as the catheter of FIG. 1A or FIG. 2A being used to access the left iliac artery from the abdominal aorta, according to embodiments of the present disclosure;

FIG. 9A shows a lateral (side) arteriographic image of the abdominal aorta and major branch arteries, including the celiac artery and the superior mesenteric artery;

FIG. 9B shows a schematic lateral image of the abdominal aorta and major branch arteries, as well as the catheter of FIG. 1A or FIG. 2A being used to access the celiac artery from the supraceliac abdominal aorta, according to embodiments of the present disclosure; and FIG. 9C shows a schematic lateral image of the abdominal aorta and major branch arteries, as well as the catheter of FIG. 1A or FIG. 2A being used to access the superior mesenteric artery from the supraceliac abdominal aorta, according to embodiments of the present disclosure.

DETAILED DESCRIPTION

Figure 1A:
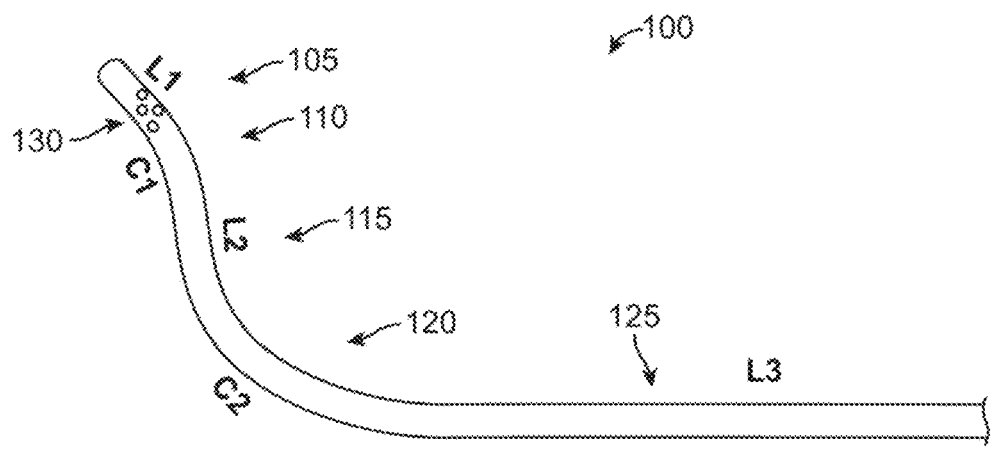
FIG. 1A shows a side view of a dual-curved catheter according to embodiments of the present disclosure.
Figure 1B:
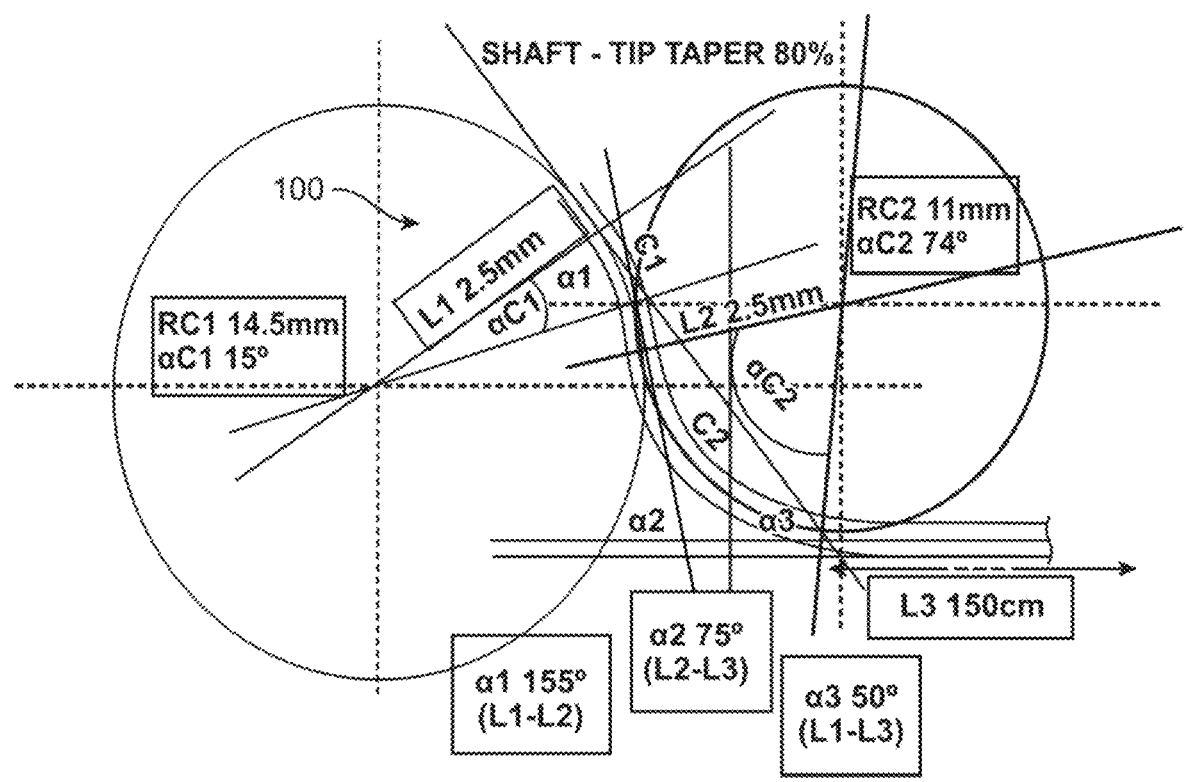
FIG. 1B shows a side view of the catheter of FIG. 1A with labelling to show its angles of curvature and lengths of various portions.

FIGS. 1A and 1B show a dual-curved catheter 100 according to first embodiments of the present disclosure. The catheter 100 will typically comprise a distal portion 105, a primary curved portion 110 proximal of the distal portion 105, an elongate transition portion 115 proximal of the primary curved portion 110, a secondary curved portion 120 proximal of the transition portion 115, and an elongate proximal portion 125 proximal of the secondary curved portion 120. The distal portion 105 may include a plurality of side ports 130 near or at the distal portion 105. The side ports allow use of the same catheter for aortography without a catheter exchange. The distal portion 105 may be tapered. The distal portion 105 may be soft and atraumatic. The tapered and caudo-laterally oriented distal portion 105 may facilitate selective vessel catheterization and/or crossing a stenosis or an occlusion. Elongate proximal portion 125 may be biased to be straight. The catheter 100 may be made of a relatively soft and compliant material to minimize contact injury during advancement and other manipulations of the catheter 100 within the vasculature, though the catheter 100 may be biased to assume the dual-curved configuration when unconstrained or not straightened by a straightening or relatively non-compliant guidewire. The catheter 100 may be made of a braided and/or otherwise reinforced material to provide torqueability. The material of the catheter 100 will typically be resiliently deformable enough to allow passage of catheter 100 from a radial artery all the way to the aortic arch and typically beyond, as described herein. The catheter 100 may have a hydrophilic coating extending from the catheter tip at the distal portion 105 to near the catheter hub, for example, 10 cm to 50 cm from the catheter hub, which is typically located at a proximal end of elongate proximal portion 125 of catheter 100.

FIG. 1B shows various relative angles and lengths of some first embodiments of the dual-curved catheter 100. The catheter 100 may be provided in various shape configurations and sizes, typically within the following ranges of dimensions for patient body habitus and size. The outer diameter of the catheter 100 may be from 3 to 8 French (Fr). The inner diameter of the catheter 100 may be from 0.014 inches to 0.038 inches, or greater than 0.038 inches in some embodiments (e.g., embodiments intended for application as a guide catheter to accommodate standard guidewire and catheter sizes, for example). The distal opening at the distal tip at the distal portion 105 may have the same size as the inner diameter of the catheter 100 (e.g., 0.014" to 0.038" or greater, for example, in some embodiments intended for application as a guide catheter to accommodate a catheter having a gauge of up to 6 or 7 Fr coaxially). The inner diameter may, for example, accommodate various sizes of guidewires and catheters (e.g., wherein the inner lumen of the catheter serves as a guidewire lumen). In some cases, the inner lumen of catheter 100 may serve as an injection lumen, e.g., in addition to containing various sizes of guidewires and catheters. The length of the shaft of the catheter 100, e.g., the elongate proximal portion 125, may be from 80 to 200 cm. In some cases, the elongate portion 125 of catheter 100 is at least 80 cm or at least 200 cm. For example, elongate portion 125 may be 80, 100, 125, 150, or 200 cm in length. In some cases, the catheter has an overall length of 80 to 200 cm or 100 to 150 cm. The distal portion 105 may be tapered from the remaining body of the catheter. As shown in FIGS. 1A and 1B, an optimal range of the tapering may be from 70% to 85%, for example, 80%. In some embodiments, the tapering may extend to at least a part of the primary curved portion 110 of the catheter and optionally even more proximally (e.g., extending to or near transition portion 115, secondary curved portion 120, or elongate proximal portion 125. All or a portion of catheter 100 may be soft and flexible. In some embodiments, the catheter 100 may uniformly soft and flexible throughout its length. Alternatively, the catheter 100 may be progressively softer or more flexible than the main catheter shaft toward the tip.

Referring back to FIG. 1B, various angles and lengths of the portions of the first embodiment of the catheter 100 are shown. The distal portion 105 may have a length (L1) of from 1 to 7 mm, preferably 2 to 6 mm, for example, 2.5 mm. The transition portion 115 may have a length (L2) of from 1 to 8 mm, preferably 2 to 7 mm, for example, 2.5 mm. The elongate proximal portion 125 may have a length (L3) of between 80 to 200 cm, for example, 150 cm. The first curved portion 110 may have a radius of curvature (RC1) of from 10 to 20 mm, preferably 12 to 17 mm, for example 14.5 mm or 15 mm. The first curved portion 110 may have a length of 2 to 8 mm, for example, 3 to 7 mm. The second curved portion 120 may have a radius of curvature (RC2) of from 7 to 15 mm, preferably 8 to 13 mm, for example, 11 mm. The second curved portion 120 may have a length of 4 to 20 mm, for example, 5 to 17 mm. The angle of curvature of the first curved portion 110 (αC1) may be between 10° to 30°, preferably 12° to 17°, for example 15°. The angle of curvature of the second curved portion 120 (αC2) may be between 50° to 90°, preferably 60° to 80°, for example 74°. The angle between the distal portion 105 and the transition portion 115 (α1) may be between 120° to 170°, preferably 140° to 160°, for example 155°. The angle between the transition portion 115 and the elongate proximal portion 125 (α2) may be between 90° to 125°, preferably 95° to 115°, for example 105°. The angle between the distal portion 105 and the proximal portion 125 (α3) may be between 95° to 150°, preferably 105° to 140°, for example 130°. These dimensions may be adjusted proportionally for pediatric application embodiments.

Figure 2A:
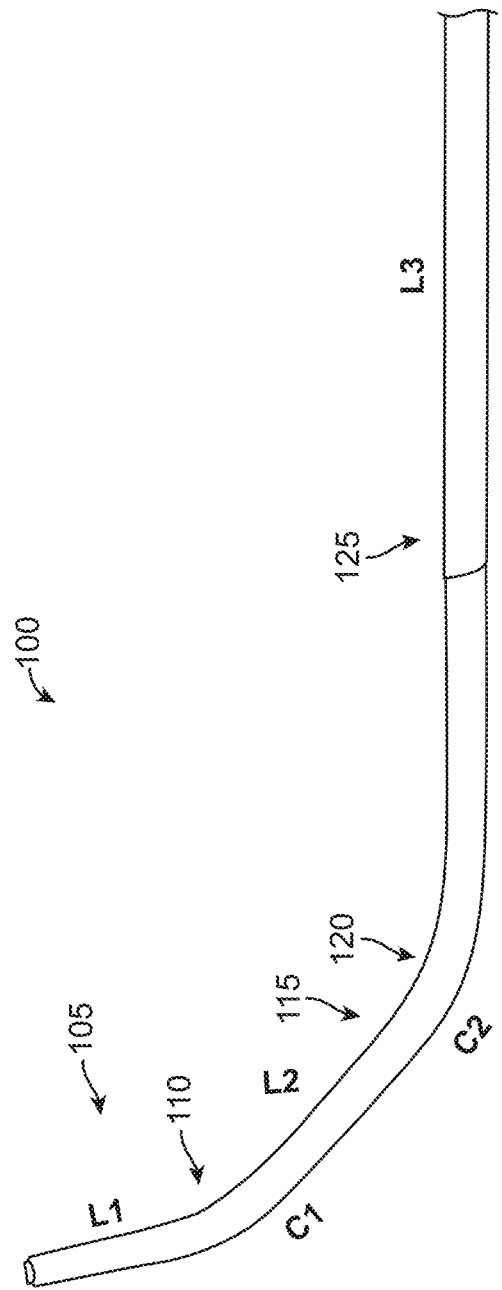
FIG. 2A shows a side view of a dual-curved catheter according to further embodiments of the present disclosure.
Figure 2B:
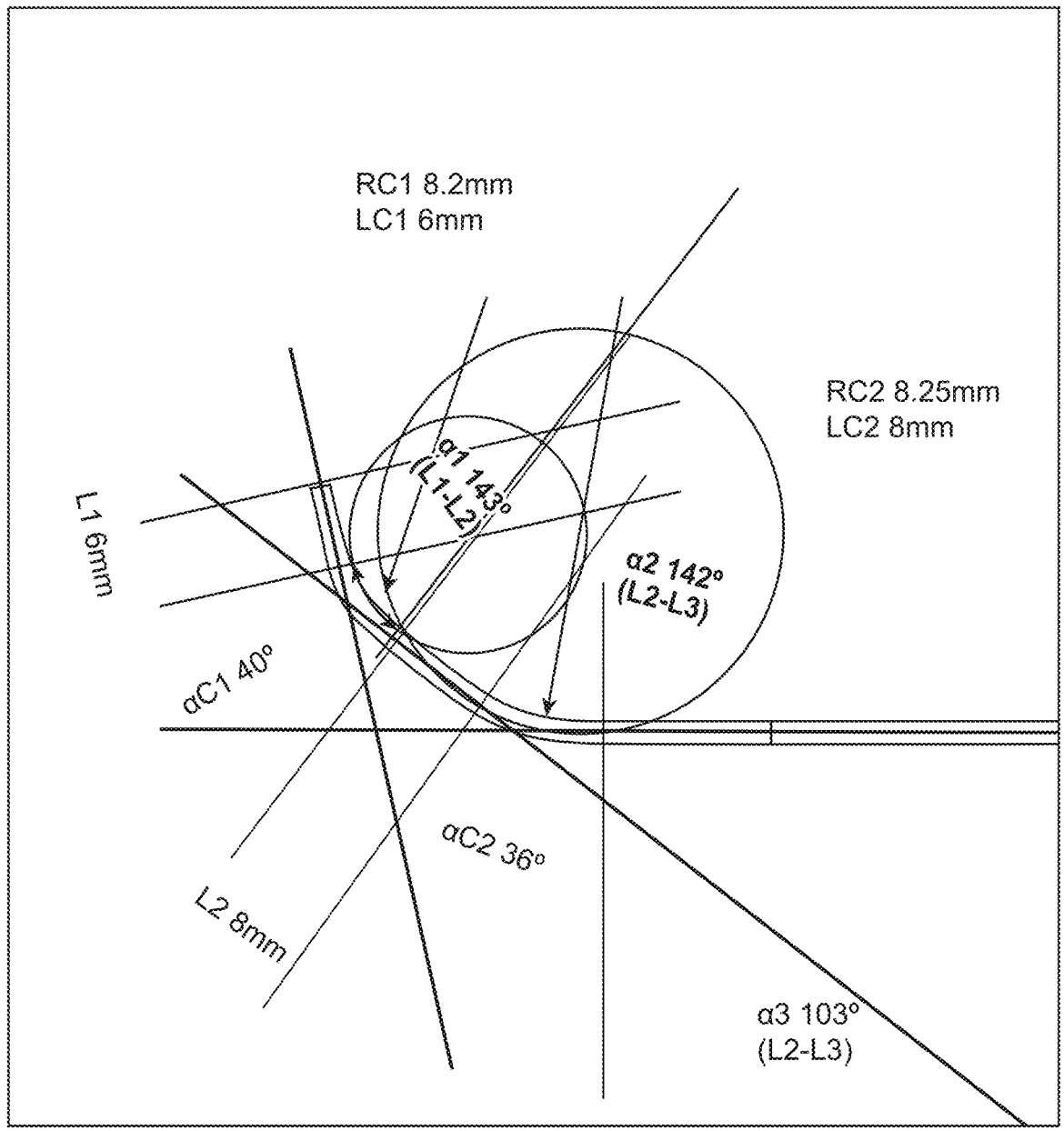
FIG. 2B shows a side view of the catheter of FIG. 2A with labelling to show its angles of curvature and lengths of various portions.

FIGS. 2A and 2B show the dual-curved catheter 100 according to second embodiments of the present disclosure.

Referring to FIG. 2A, the catheter 100 will typically comprise a distal portion 105, a primary curved portion 110 proximal of the distal portion 105, an elongate transition portion 115 proximal of the primary curved portion 110, a secondary curved portion 120 proximal of the transition portion 115, and an elongate proximal portion 125 proximal of the secondary curved portion 120. Though not shown in FIG. 2A, the distal portion 105 of some second embodiments of catheter 100 may include a plurality of side ports near or at the distal portion 105 (e.g., as shown in FIG. 1A with respect to some first embodiments of catheter 100). The side ports in second embodiments of catheter 100 allow use of the same catheter for aortography without a catheter exchange. The distal portion 105 may be tapered. The distal portion 105 may be soft and atraumatic. The tapered and caudo-laterally oriented distal portion 105 may facilitate selective vessel catheterization and/or crossing a stenosis or an occlusion. The catheter 100 may be made of a relatively soft and compliant material in some second embodiments of catheter 100 to minimize contact injury during advancement and other manipulations of the catheter 100 within the vasculature, though the catheter 100 may be biased to assume the dual-curved configuration when unconstrained or not straightened by a straightening or relatively non-compliant guidewire. The catheter 100 may be made of a braided and/or otherwise reinforced material in some second embodiments of catheter 100, e.g., to provide torqueability. The material of the catheter 100 will typically be resiliently deformable enough to allow passage of catheter 100 from a radial artery all the way to the aortic arch and typically beyond, as described herein. The catheter 100 may have a hydrophilic coating extending from the catheter tip at the distal portion 105 to near the catheter hub, for example, 10 cm to 50 cm from the catheter hub, which is typically located at a proximal end of proximal portion 125 of catheter 100.

FIG. 2B shows various relative angles and lengths of some second embodiments of the dual-curved catheter 100. The catheter 100 may be provided in various shape configurations and sizes, typically within the following ranges of dimensions for patient body habitus and size. The outer diameter of the catheter 100 may be from 3 to 8 French (Fr). The inner diameter of the catheter 100 may be from 0.014 inches to 0.038 inches, or greater than 0.038 inches in some embodiments (e.g., embodiments intended for application as a guide catheter to accommodate standard guidewire and catheter sizes, for example). The distal opening at the distal tip at the distal portion 105 may have the same size as the inner diameter of the catheter 100 (e.g., 0.014" to 0.038" or greater, for example, in some embodiments intended for application as a guide catheter to accommodate a catheter having a gauge of up to 6 or 7 Fr coaxially). The inner diameter may, for example, accommodate various sizes of guidewires and catheters (e.g., wherein the inner lumen of the catheter serves as a guidewire lumen). In some cases, the inner lumen of catheter 100 may serve as an injection lumen, e.g., in addition to containing various sizes of guidewires and catheters. The length of the shaft of the catheter 100, e.g., the elongate proximal portion 125, may be from 80 to 200 cm. In some cases, the elongate portion 125 of catheter 100 is at least 80 cm or at least 200 cm. For example, elongate portion 125 may be 80, 100, 125, 150, or 200 cm in length. In some cases, the catheter has an overall length of 80 to 200 cm or 100 to 150 cm. The distal portion 105 may be tapered from the remaining body of the catheter. As shown in FIGS. 1A and 1B, an optimal range of the tapering may be from 70% to 85%, for example, 80%. In some embodiments, the tapering may extend to at least a part of the primary curved portion 110 of the catheter and optionally even more proximally (e.g., extending to or near transition portion 115, secondary curved portion 120, or elongate proximal portion 125. All or a portion of catheter 100 may be soft and flexible. In some embodiments, the catheter 100 may uniformly soft and flexible throughout its length. Alternatively, the catheter 100 may be progressively softer or more flexible than the main catheter shaft toward the tip.

Referring back to FIG. 2B, various angles and lengths of the portions of this embodiment of the catheter 100 are shown. The distal portion 105 may have a length (L1) of from 1 to 7 mm, preferably 2 to 6 mm, for example, 2.5 mm. The transition portion 115 may have a length (L2) of from 1 to 8 mm, preferably 2 to 7 mm, for example, 2.5 mm. The elongate proximal portion 125 may have a length (L3) of between 80 to 200 cm, for example, 150 cm. The first curved portion 110 may have a radius of curvature (RC1) of from 10 to 20 mm, preferably 12 to 17 mm, for example 14.5 mm or 15 mm. The first curved portion 110 may have a length of 2 to 8 mm, for example, 3 to 7 mm. The second curved portion 120 may have a radius of curvature (RC2) of from 7 to 15 mm, preferably 8 to 13 mm, for example, 11 mm. The second curved portion 120 may have a length of 4 to 20 mm, for example, 5 to 17 mm. The angle of curvature of the first curved portion 110 ($\alpha C1$) may be between 10° to 30°, preferably 12° to 17°, for example 15°. The angle of curvature of the second curved portion 120 ($\alpha C2$) may be between 50° to 90°, preferably 60° to 80°, for example 74°. The angle between the distal portion 105 and the transition portion 115 ($\alpha 1$) may be between 120° to 170°, preferably 140° to 160°, for example 155°. The angle between the transition portion 115 and the elongate proximal portion 125 ($\alpha 2$) may be between 90° to 125°, preferably 95° to 115°, for example 105°. The angle between the distal portion 105 and the proximal portion 125 ($\alpha 3$) may be between 95° to 150°, preferably 105° to 140°, for example 130°. These dimensions may be adjusted proportionally for pediatric application embodiments.

Table 1 below shows a comparison between exemplary dimensions of the first and second embodiments of the catheters.

TABLE 1

| | Embodiment 1 | | | Embodiment 2 | | |
|---|---|---|---|---|---|---|
| | Range | Preferred | Actual | Range | Preferred | Actual |
| L1 | 1-7 mm | 2-6 mm | 2.5 mm | 1-7 mm | 2-6 mm | 6 mm |
| L2 | 1-8 mm | 2-7 mm | 2.5 mm | 2-10 mm | 2-10 mm | 8 mm |
| L3 | 80-200 | 80-200 | 150 mm | 80-200 mm | 80-200 mm | 150 mm |
| LC1 | 2-8 mm | 3-7 mm | 4 mm | 3-12 mm | 4-11 mm | 6 mm |
| LC2 | 4-20 mm | 5-17 mm | 14 mm | 3-15 mm | 4-12 mm | 8 mm |
| a1° (L1-L2) | 120-170° | 140-160° | 155° | 110-160° | 120-155° | 143° |
| A2° (L2-L3) | 90-125° | 95-115° | 105° | 110-160° | 120-155° | 142° |
| A3° (L1-L3) | 95-150° | 105-140° | 130° | 80-130° | 90-120° | 103° |

TABLE 1-continued

| | Embodiment 1 | | | Embodiment 2 | | |
|---|---|---|---|---|---|---|
| | Range | Preferred | Actual | Range | Preferred | Actual |
| RC1 | 10-20 mm | 12-17 mm | 14.5 mm | 5-15 mm | 6-13 mm | 8.2 mm |
| RC2 | 7-18 mm | 8-13 mm | 11 mm | 5-15 mm | 6-13 mm | 8.25 mm |
| aC1° | 10-30° | 12-17° | 15° | 20-60° | 30-50° | 40° |
| aC2° | 50-90° | 60-80° | 74° | 20-60° | 30-50° | 36° |

Length of Curved Segment (LC)
Radius of Curvature (RC)
Degree or Angle of Curvature (αC)
Length of Straight Segment (L)
Angle between Straight Segments (α)

The catheter 100 may have any number of side ports 130. In some cases, the catheter 100 will have one or more side ports 130. The catheter 100 will typically have 0 to 6 side ports 130. If the catheter 100 is used as flush catheter or as both a selective and flush catheter, at least 2 to 6 side ports 130 may be preferable. If the catheter 100 is used as a selective catheter only, 0 to 2 side ports 130 may be preferable. The location and distribution of the side ports 130 may be varied as well. While FIGS. 1A and 1B show the side ports 130 positioned at the distal portion 105, the side ports 130 may be provided in any portion of the catheter 100, including the first curved portion 110, the transition portion 115, the second curved portion 120, and the proximal portion 125. The side ports 130 may be non-laterally opposed and/or spirally arranged. The shape and/or diameter or width of the side ports 130 may vary. In some embodiments, the side ports 130 may have a diameter of 0.018" to 0.038". The side ports 130 will typically be round, but may be oval, triangular, square, rectangular, or have other shapes.

Figure 3A:
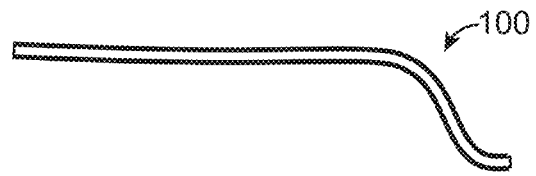
FIGS. 3A-3E show side views of the catheter of FIG. 1A having different guidewires advanced through the lumen of the catheter.
Figure 3B:
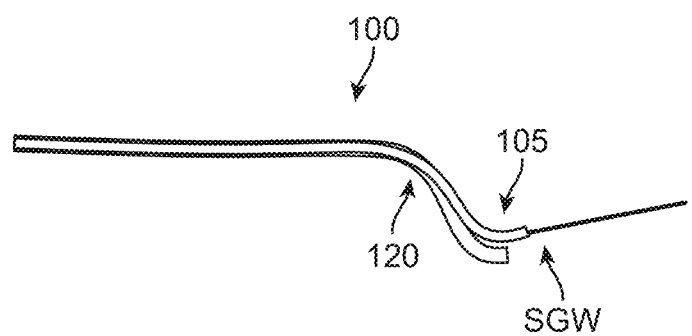
Figure 3C:
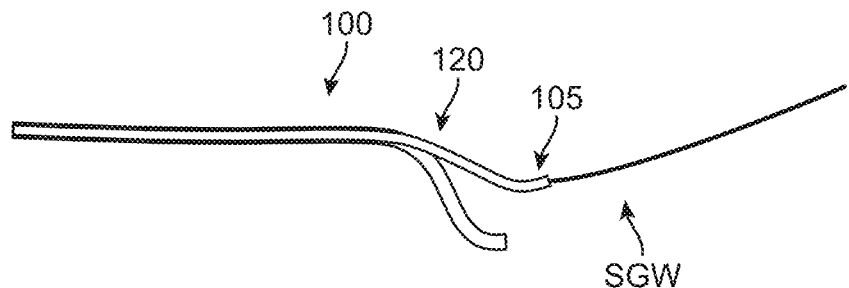

As shown in FIGS. 3A-3E, various guidewires may be advanced through the lumen of the catheter 100 depending on the tip configuration and stiffness desired for various maneuvers. FIG. 3A shows the catheter 100 without any guidewire advanced therethrough or advanced only through to its proximal portion 125. FIG. 3B shows a relatively "stiff" tip straightening guidewire SGW advanced through the catheter 100, increasing the radii of curvature of the first and/or secondary curved portions 105, 120 (compare catheter position compared to outline of original catheter position in FIG. 3B). For example, the relatively "stiff" tip straightening guidewire SGW (and/or its stiffer portion only) may be advanced to just short or partially into of the first and/or second curved portions 105, 120, thereby partially or completely straightening the first and/or secondary curved portions 105, 120. FIG. 3C shows the relatively "stiff" tip straightening guidewire SGW further advanced through the catheter 100, further increasing the radii of curvature of the first and secondary curved portions 105, 120 (compare catheter position compared to outline of original catheter position in FIG. 3C). In this manner, the caudo-lateral angle of the distal portion 105 can be adjusted. Shaped stiffening guidewires may also be used with the catheter 100.

Figure 3D:
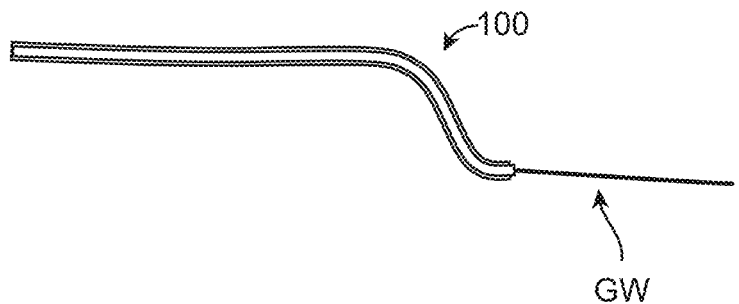
Figure 3E:
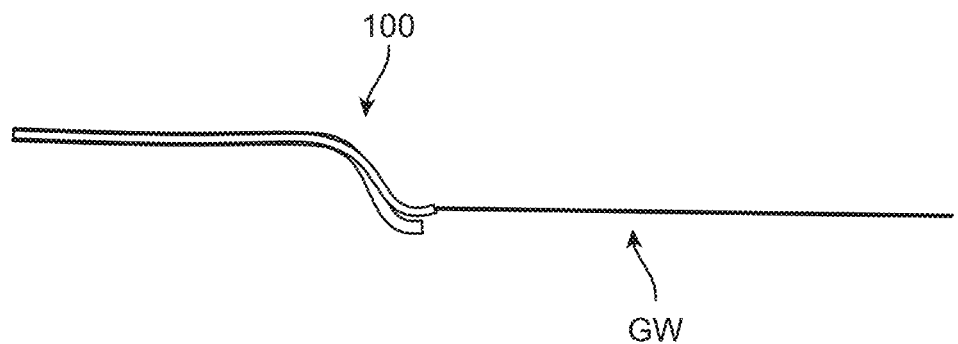

Non-straightening "floppy" soft tip guidewires may also be used. FIG. 3D shows a non-straightening guidewire GW being advanced through the catheter 100 with minimal effect to the curvature (compare catheter position compared to outline of original catheter position in FIG. 3D), and FIG. 3E shows the guidewire GW further advanced through the catheter 100, again with minimal effect to the curvature (compare catheter position compared to outline of original catheter position in FIG. 3E). In many embodiments, the guidewire used will be a soft-tip Bentson-type guidewire as known in the art.

The dual-curved catheters disclosed herein will typically be configured to be introduced into the vasculature of a patient or subject via radial access, e.g., through a percutaneous puncture (e.g., Seldinger technique) to access the radial artery RA at the wrist WR of the patient PT. Radial access may be advantageous in that normal antegrade blood flow can be only minimally decreased during the procedure, and even if, rarely, the radial artery is severely compromised, collateral blood flow to the radial artery and the hand is maintained through the deep and superficial palmar arches PUA from the ulnar artery UA, whereas a complication at a brachial access will usually, at least acutely, more severely reduce downstream collateral blood flow from above. Also, bleeding from a radial access site after catheterization can be more easily controlled at the wrist than at a brachial access site, thus a hematoma compressing, and potentially damaging nerves and other adjacent structures is significantly less likely to occur at a radial entry site.

Figure 4:
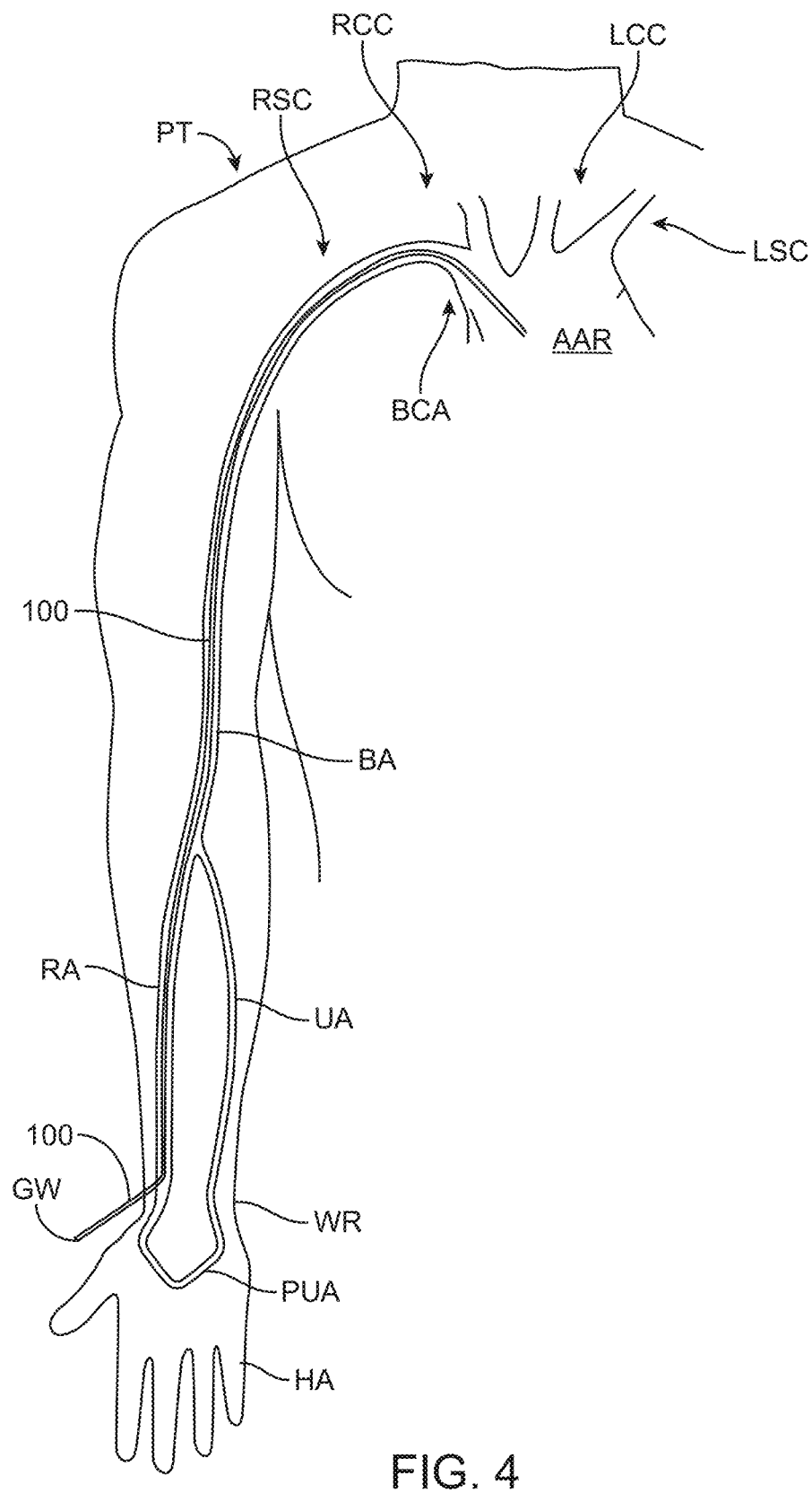
FIG. 4 shows the catheter of FIG. 1A or FIG. 2A being advanced to the aortic arch by radial artery access.

FIG. 4 shows a catheter 100 being advanced to the aortic arch AAR via right radial artery access. FIG. 4 shows the hand HA, wrist WR, and various arteries of the patient PT, including the palmar arches PUA, radial artery RA, ulnar artery UA, brachial artery BA, right subclavian artery RSC, right common carotid artery RCC, brachiocephalic artery BCA, left common carotid artery LCC, left subclavian artery LSC, and the aortic arch AAR. As shown in FIG. 4, the catheter 100 may be advanced up through the radial artery RA, through the brachial artery BA, through the right subclavian artery RSC, and through the brachiocephalic artery BCA to access the aortic arch AAR. In many embodiments, a guidewire GW is first advanced through these arterial structures before or concurrently with the catheter 100 being advanced over the guidewire GW. In some embodiments, the guidewire GW may at least partially straighten the catheter 100 to facilitate its advancement through the vasculature. In some embodiments, a straightening guidewire SGW may be used to facilitate introduction of the catheter 100 to the aortic arch and then exchanged for a non-straightening guidewire GW to facilitate further use and maneuvering of the catheter 100 as described herein.

While FIG. 4 shows radial access to the patient PT through the right wrist, the vasculature of the patient may also be via radial access from the left wrist, and the catheter 100 may be advanced into the aortic arch AAR through the left subclavian artery LSC. While radial access is described herein, the catheter 100 may also be introduced into the vasculature in other ways, including via other arterial access (e.g., via an axillary artery, a brachial artery, a femoral artery, a carotid artery, a tibial artery, or the like), or venous access (e.g., via a forearm vein, a brachial vein, an axillary vein, a jugular vein, a femoral vein, a popliteal vein, or the like).

Figure 5A:
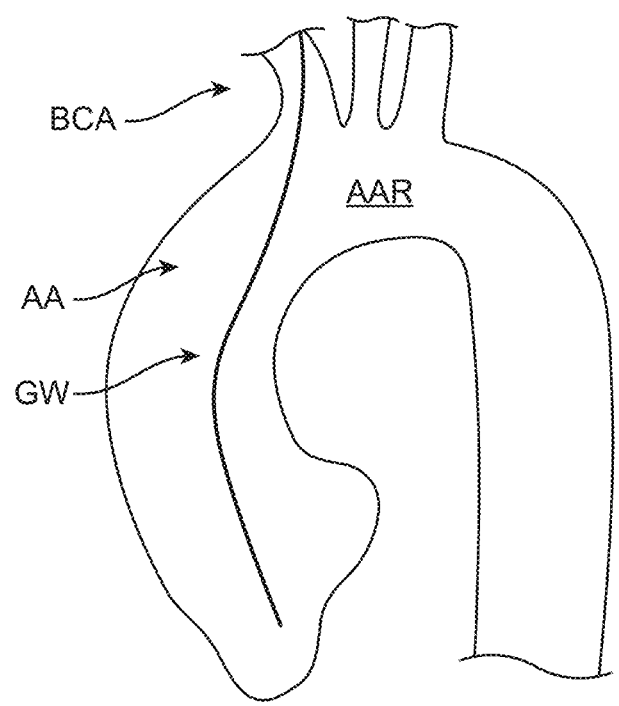
FIGS. 5A-5F show left anterior oblique projection (side) views of the catheter of FIG. 1A or FIG. 2A being used to access both the ascending aorta and the descending aorta from the right brachiocephalic artery, according to embodiments of the present disclosure.
Figure 5B:
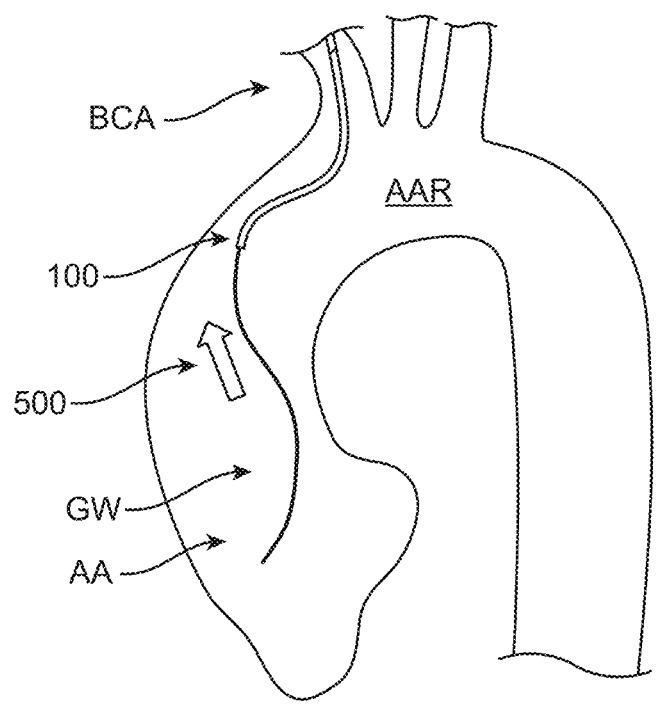
Figure 5C:
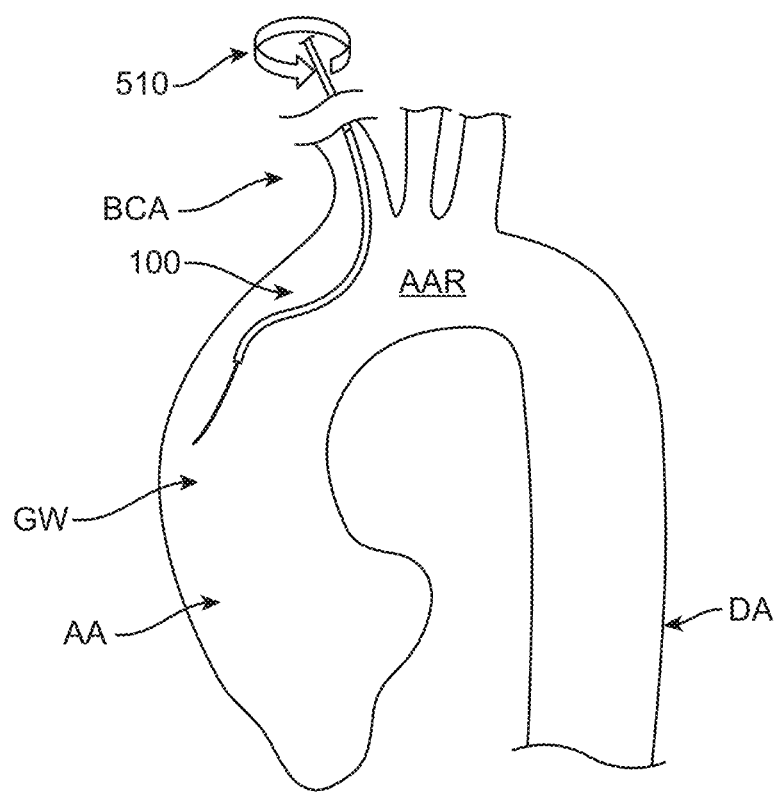
Figure 5D:
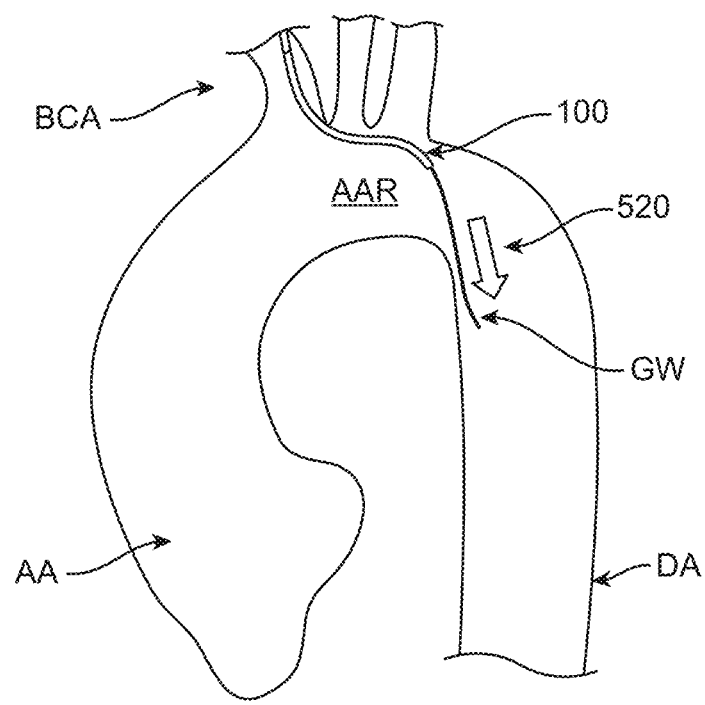
Figure 5E:
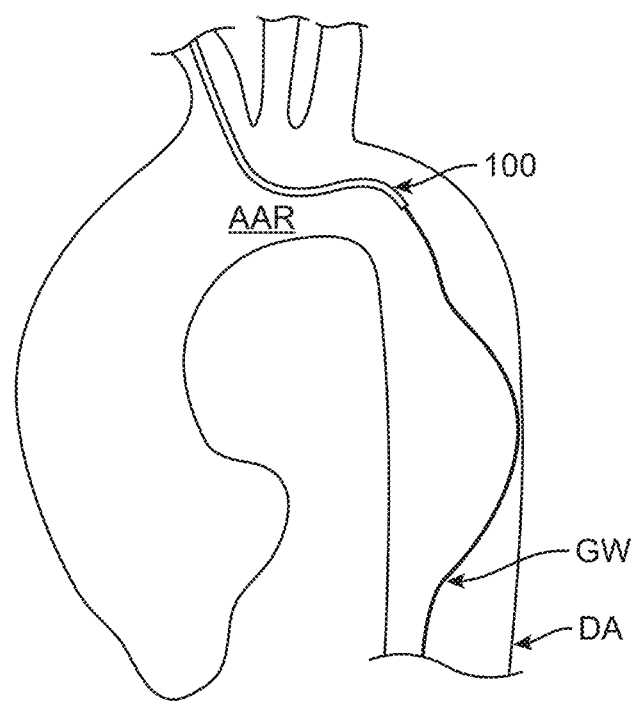
Figure 5F:
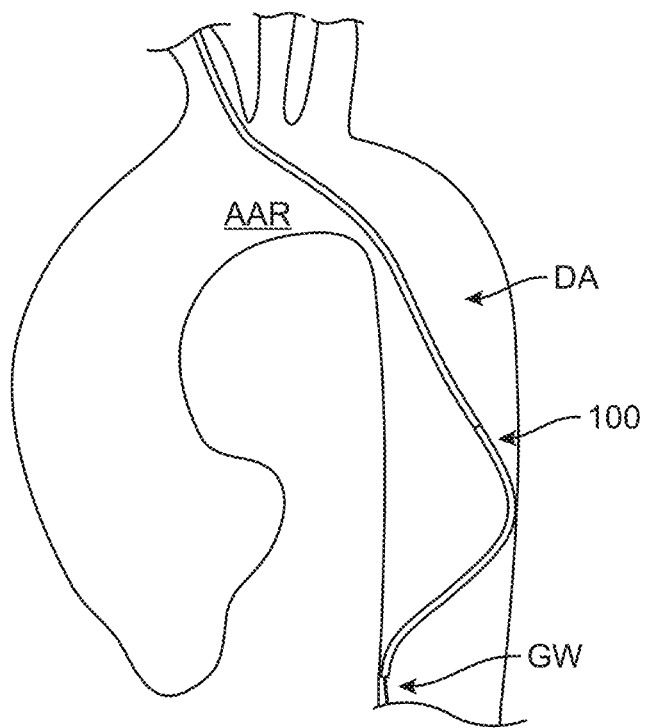

Particular methods of using the dual-curved catheter 100 are now described. As shown in FIG. 5A, an exemplary method may start with a guidewire GW being advanced through the brachiocephalic artery (BCA), through the aortic arch AAR, and into the ascending aorta AA (e.g., at or adjacent the ascending aorta AA, optionally with a distal port of the catheter oriented toward the ascending aorta AA). As shown in FIG. 5B, the catheter 100 may be advanced over the guidewire GW and into the aortic arch AAR while being oriented toward the ascending aorta AA. There, various fluids and/or agents may be introduced to the ascending aorta AA via the side ports of the catheter 100, in some cases. The guidewire GW may be retracted into the catheter 100 leaving only a few (e.g., 1-5) centimeters (cm) of soft floppy tip extending from the catheter in the direction indicated by arrow 500. As shown in FIG. 5C, the catheter 100 may be rotated or torqued to reverse its orientation from toward the ascending aorta AA to toward the descending aorta DA (e.g., advanced until at or adjacent the descending aorta DA, optionally with a distal port of the catheter oriented toward the descending aorta DA), as indicated by arrow 510. The rotation may be a rotation of about 180°. The rotation may be clockwise or counterclockwise. The length of guidewire GW extending from the catheter (which may be a few, e.g., 1-5, centimeters) may be relatively soft to minimize contact injury to the walls of the aortic arch AAR and other nearby vascular structures as the rotation occurs. The particular curvatures and relative lengths of the catheter 100 may allow its use to access both the ascending aorta AA and the descending aorta DA, with minimal interference with vascular structures as the catheter 100 is rotated. In many known procedures, separate catheters must be used to separately access the ascending aorta AA and the descending aorta DA, perform an aortogram and thereafter perform selective and subselective aortic branch catheterizations, which often requires an exchange of the catheter over the guidewire at its location. The ability of the catheter 100 to simply be rotated to access the ascending aorta AA or the descending aorta DA as well as perform aortography and selective and subselective aortic branch catheterizations may obviate the need for at least one catheter exchange, which may otherwise present an injury risk to the patient PT or at least be cumbersome for the operator. As shown in FIG. 5D, the rotation of the catheter 100 to the orientation toward the descending aorta DA also orients the guidewire GW toward the descending aorta DA, and the guidewire GW may be advanced into the descending aorta DA in the direction indicated by arrow 520. FIG. 5E shows the guidewire GW further advanced through the descending aorta DA. As shown in FIG. 5F, the catheter 100 can be further advanced over the guidewire GW into the descending aorta DA. In some embodiments, the catheter 100 may be advanced further into the abdominal aorta ABA (not shown in FIG. 5F) including those of the lower extremities for further use therein as described herein.

Although the above steps described with respect to FIGS. 5A-5F show methods of using the catheter 100 in accordance with many embodiments, a person of ordinary skill in the art will recognize many variations based on the teaching described herein. The steps may be completed in a different order (for example, with the descending aorta DA being accessed first instead of the ascending aorta AA). Steps may be added or deleted. Some of the steps may comprise sub-steps. Many of the steps may be repeated as often as beneficial.

Figure 6A:
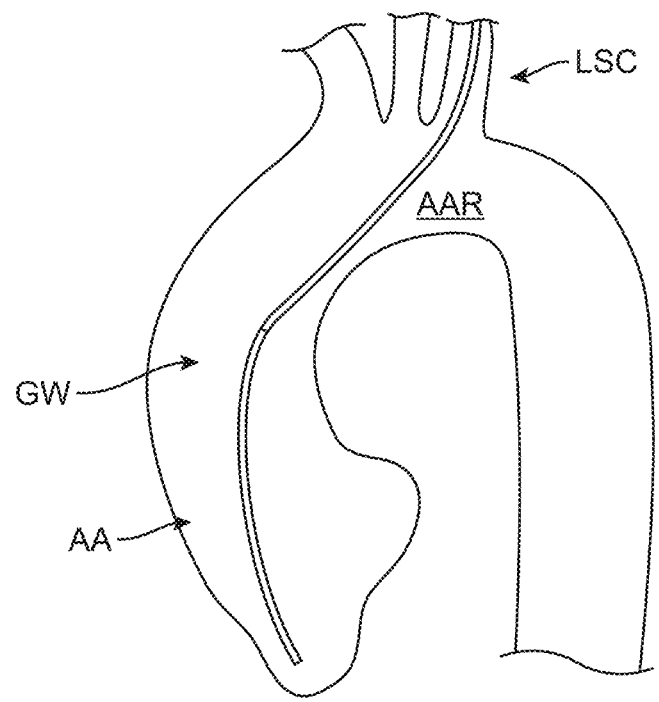
FIGS. 6A-6F show left anterior oblique projection (side) views of the catheter of FIG. 1A or FIG. 2A being used to access both the ascending aorta and the descending aorta from the left subclavian artery, according to embodiments of the present disclosure.
Figure 6B:
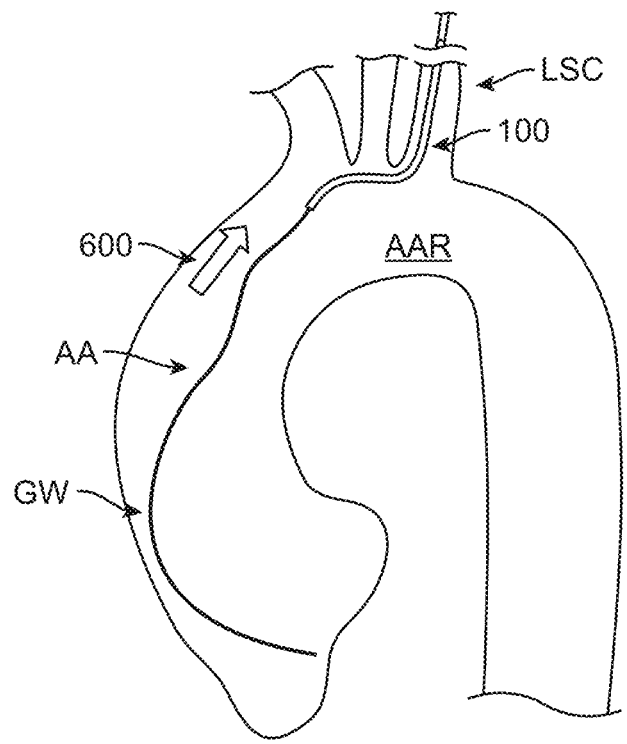
Figure 6C:
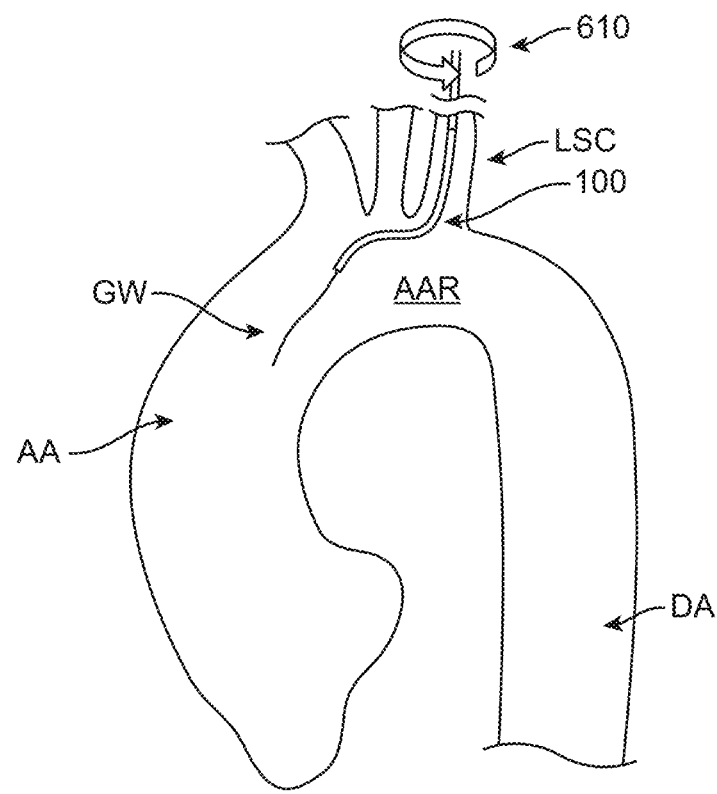
Figure 6D:
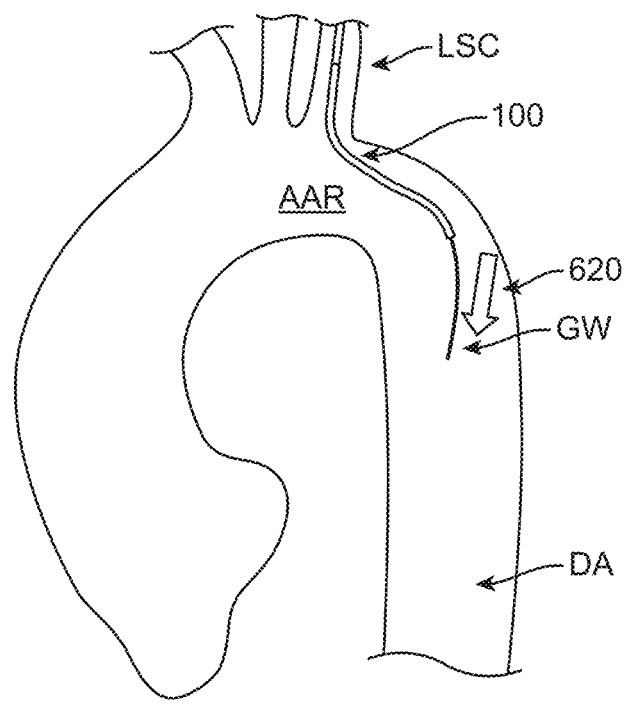
Figure 6E:
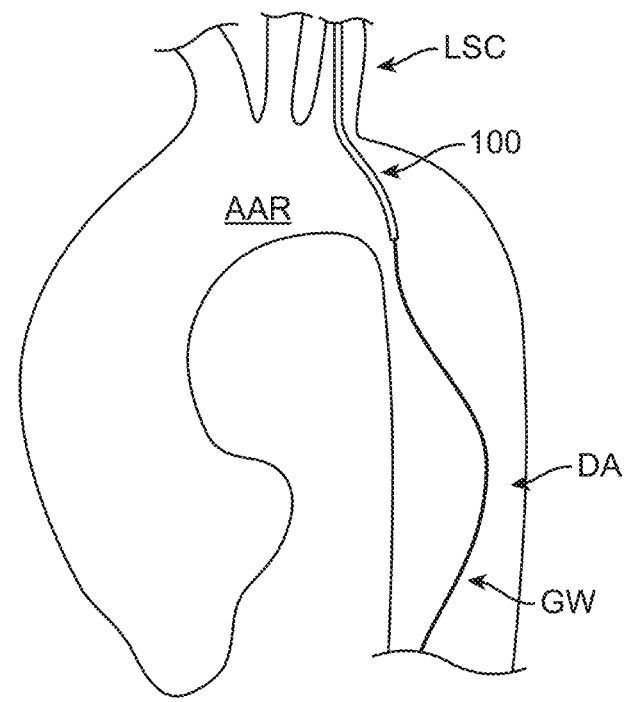
Figure 6F:
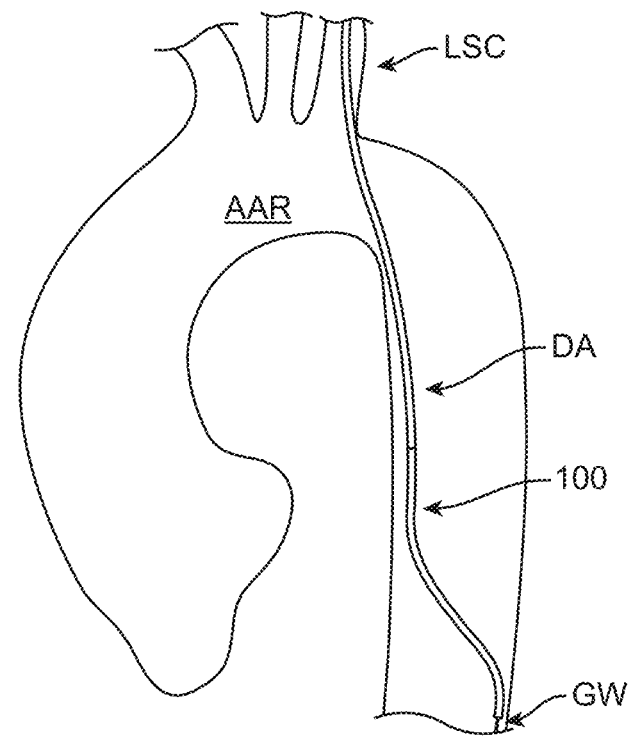

FIGS. 6A-6F show an exemplary method similar to that described with respect to FIGS. 5A-5F, but with the catheter 100 being advanced into the aortic arch AAR from the left subclavian artery LSC. As shown in FIG. 6A, the exemplary method may start with a guidewire GW being advanced through the left subclavian artery LSC, through the aortic arch AAR, and into the ascending aorta AA. As shown in FIG. 6B, the catheter 100 may be advanced over the guidewire GW and into the aortic arch AAR while being oriented toward the ascending aorta AA. There, various fluids and/or agents may be introduced to the ascending aorta AA via the side ports of the catheter, in some cases. The guidewire GW may be (nearly completely) retracted into the catheter 100 in the direction indicated by arrow 600. As shown in FIG. 6C, the catheter 100 may be rotated or torqued to reverse its orientation from toward the ascending aorta AA to toward the descending aorta DA, as indicated by arrow 610. The rotation may be of about 180°. The rotation may be clockwise or counterclockwise. As shown in FIG. 6D, the rotation of the catheter 100 to the orientation toward the descending aorta DA also orients the guidewire GW toward the descending aorta DA, and the guidewire GW may be advanced into the descending aorta. FIG. 6E shows the guidewire GW further advanced through the descending aorta DA. As shown in FIG. 6F, the catheter 100 can be further advanced over the guidewire GW into the descending aorta DA. In some embodiments, the catheter 100 may be advanced further into the abdominal aorta ABA (not shown in FIG. 6F) for further use therein as described herein.

Although the above steps described with respect to FIGS. 6A-6F show a particular method of using the catheter 100 in accordance with many embodiments, a person of ordinary skill in the art will recognize many variations based on the teaching described herein. The steps may be completed in a different order (for example, with the descending aorta DA being accessed first instead of the ascending aorta AA). Steps may be added or deleted. Some of the steps may comprise sub-steps. Many of the steps may be repeated as often as beneficial.

Figure 7A:
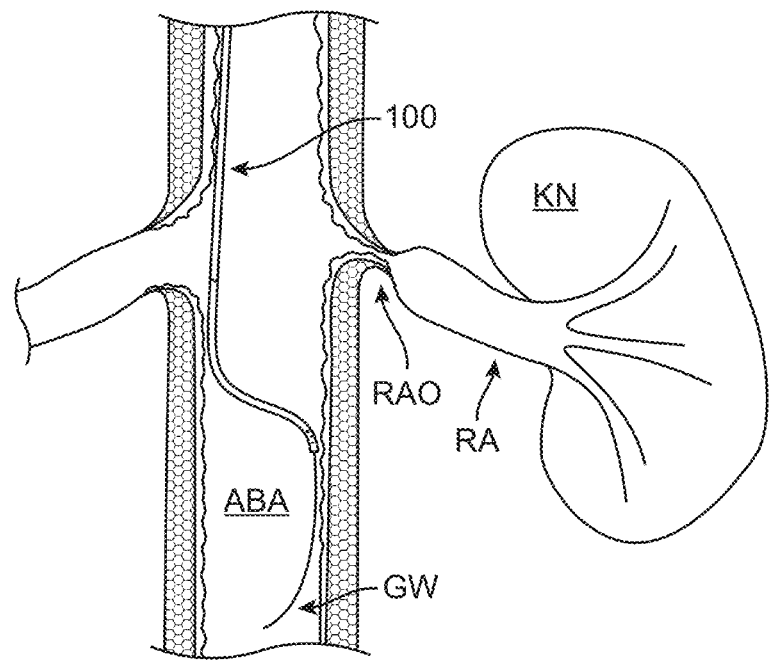
FIGS. 7A-7E show frontal projection (side) views of the catheter of FIG. 1A or FIG. 2A being used to access the stenotic (narrowed) left renal artery from a caudal position in the abdominal aorta, according to embodiments of the present disclosure.
Figure 7B:
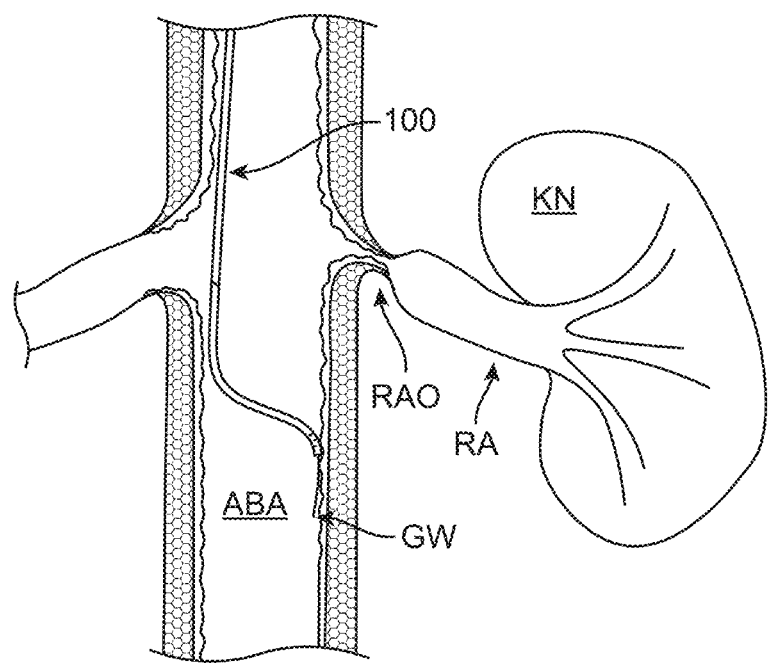
Figure 7C:
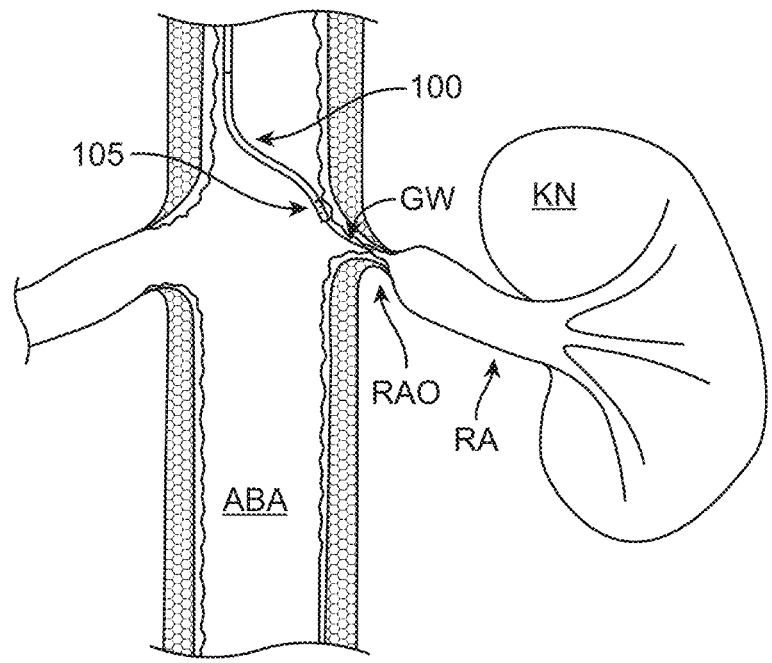
Figure 7D:
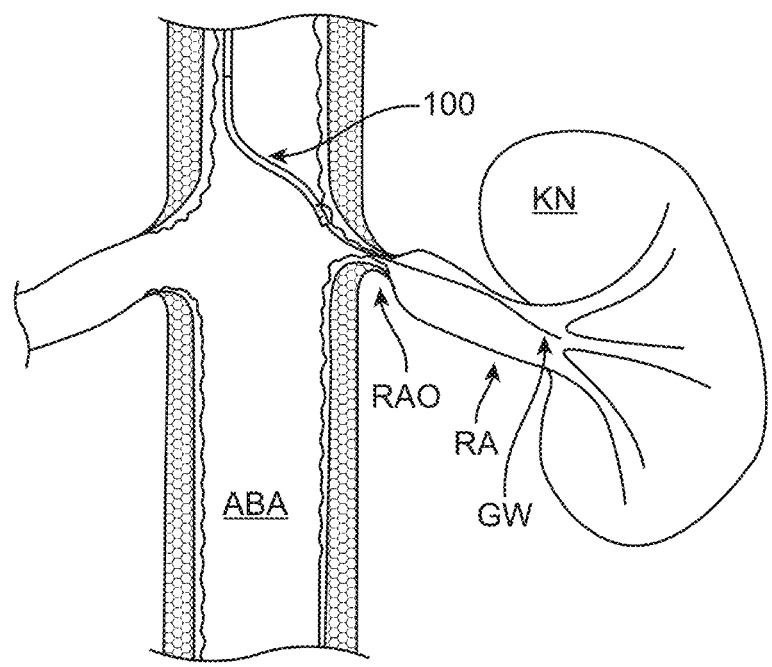
Figure 7E:
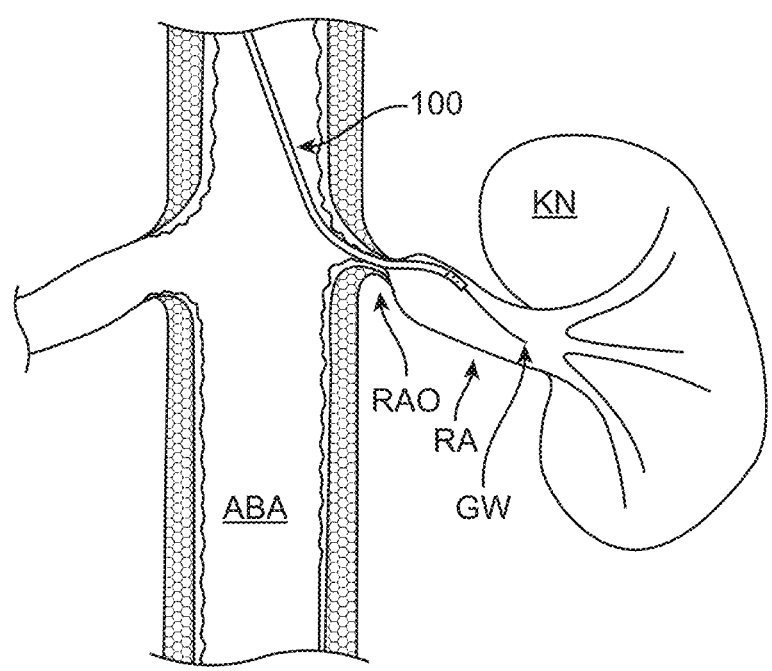
Figure 6A:
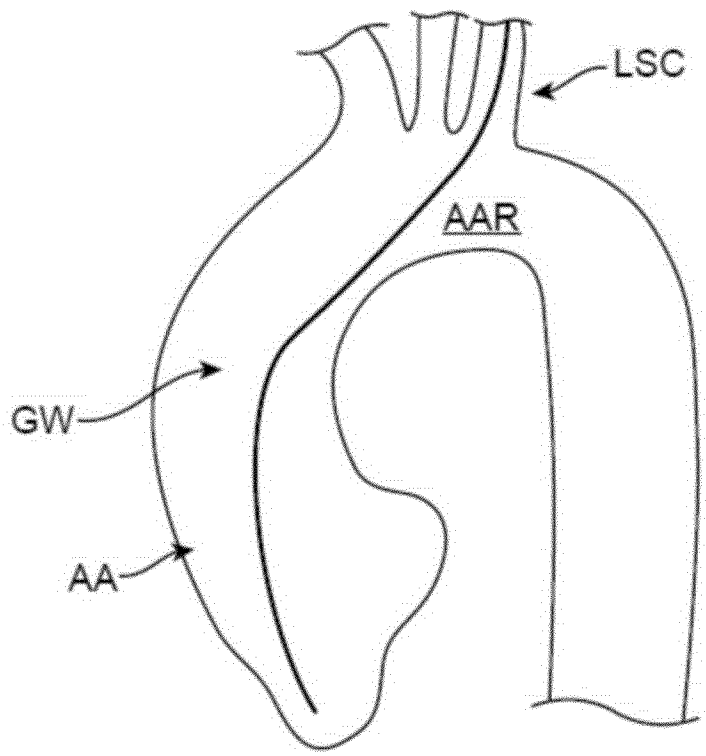

In the abdominal aorta, the catheter 100 may be used to perform an aortogram or access various branch arteries including those of the lower extremities. FIG. 7A shows the catheter 100 advanced over the guidewire GW to be positioned caudal to a kidney KN and the renal artery RA and the stenotic (narrowed) renal artery ostium RAO in the abdominal aorta ABA. As shown in FIG. 7B, the guidewire GW may be retracted almost completely into the catheter 100. As shown in FIG. 7C, the catheter 100 may be advanced and/or withdrawn within the abdominal aorta ABA so that its distal portion 105 is adjacent the renal artery ostium RAO (e.g., caudal to or cephalad of the renal artery RA), and the catheter 100 and the guidewire may be rotated or torqued into an appropriate orientation or obliquity and withdrawn until the guidewire "flicks" into and across the stenotic (narrowed) renal artery ostium RAO and enter the renal artery RA. As shown in FIG. 7D, the guidewire GW may be advanced through the catheter 100, through the renal artery ostium RAO, and into the renal artery RA. As shown in FIG. 7E, the catheter 100 may then be further advanced over the guidewire GW into the renal artery RA. In some embodiments, the guidewire GW and the guidewire 100 disposed thereover may be advanced as a single assembly into the target blood vessel.

Although the above steps described with respect to FIGS. 7A-7E show a particular method of using the catheter 100 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial.

While use of the catheter 100 to access a renal artery is described, the catheter 100 may also be used to access various other branch arteries. FIG. 8A shows an image of the abdominal aorta ABA and major branch arteries, including the right iliac artery R ILIAC (or RI), left iliac artery L ILIAC (or LI), superior mesenteric artery SMA, right renal artery R RENAL (or RR), left renal artery L RENAL (or LR), celiac artery or trunk CELIAC (or C), splenic artery S, and common hepatic artery CH. When placed in the abdominal aorta ABA, the catheter 100 may be rotated about its longitudinal axis and/or advanced or retracted within the abdominal aorta ABA to place its distal portion 105 adjacent a selected branch artery for access. For example, FIG. 8B shows the catheter 100 advanced into the right renal artery R RENAL, and FIG. 8C shows the catheter 100 advanced into the left iliac artery L ILIAC.

FIG. 9A shows an image of the abdominal aorta and major branch arteries, including the celiac artery C and the superior mesenteric artery SMA. In further examples, FIG. 9B shows the catheter 100 advanced into the celiac artery CELIAC, and FIG. 9C shows the catheter 100 advanced into the superior mesenteric artery SMA, each from the suprarenal aorta.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A catheter for accessing the ascending aorta and the descending aorta of a patient without removal from the brachiocephalic or left subclavian artery, the catheter comprising:
   (i) a distal end portion;
   (ii) a first curved portion proximal of the distal end portion, the first curved portion being biased to be curved with a first radius of curvature from 5 to 20 mm;
   (iii) a curve transition portion proximal of the first curved portion, wherein the transition portion has a length of 1 to 8 mm;
   (iv) a second curved portion proximal of the transition portion, the second curved portion being biased to be curved in a direction opposite the first curved portion and with a second radius of curvature from 5 to 15 mm; and
   (v) an elongate portion proximal of the second curved portion.

2. The catheter of claim 1, wherein the distal end portion is tapered.

3. The catheter of claim 1, further comprising a guidewire lumen.

4. The catheter of claim 1, further comprising one or more side ports.

5. The catheter of claim 1, wherein the distal end portion has a length of 1 to 7 mm.

6. The catheter of claim 1, wherein the transition portion has a length of 2 to 7 mm.

7. The catheter of claim 1, wherein the first curved portion has a length of 2 to 12 mm.

8. The catheter of claim 1, wherein the second curved portion has a length of 3 to 20 mm.

9. The catheter of claim 1, wherein the first curved portion has a curvature of 10° to 60°.

10. The catheter of claim 1, wherein the second curved portion has a curvature of 20° to 90°.

11. The catheter of claim 1, wherein the distal end portion has an angle of 110° to 170° relative to the curve transition portion.

12. The catheter of claim 1, wherein the curve transition portion has an angle of 90° to 155° relative to the elongate portion.

13. The catheter of claim 1, wherein the distal end portion has an angle of 95° to 150° relative to the elongate portion.

* * * * *

UNITED STATES PATENT AND TRADEMARK OFFICE
CERTIFICATE OF CORRECTION

PATENT NO. : 11,376,400 B2
APPLICATION NO. : 17/001950
DATED : July 5, 2022
INVENTOR(S) : Thomas A. Sos It is certified that error appears in the above-identified patent and that said Letters Patent is hereby corrected as shown below:

In the Drawings

Sheet 10, FIG. 6A, please delete and replace with attached.

Signed and Sealed this
Fourteenth Day of March, 2023

Katherine Kelly Vidal
*Director of the United States Patent and Trademark Office*